US012625046B2

(12) United States Patent
Wang et al.

(10) Patent No.: US 12,625,046 B2
(45) Date of Patent: May 12, 2026

(54) UNDERGROUND ENGINEERING ROCK MASS SHEAR SIMULATION TEST DEVICE, TEST METHOD AND TEST MACHINE THEREOF

(71) Applicants:FUJIAN UNIVERSITY OF TECHNOLOGY, Fuzhou (CN); SHANDONG UNIVERSITY OF SCIENCE AND TECHNOLOGY, Qingdao (CN); FUZHOU UNIVERSITY, Fuzhou (CN)

(72) Inventors: Gang Wang, Fuzhou (CN); Pengju Wang, Qingdao (CN); Peng He, Qingdao (CN); Xuezhen Wu, Fuzhou (CN); Kerui Fan, Qingdao (CN); Changsheng Wang, Qingdao (CN); Zhijia You, Fuzhou (CN); Ning Yang, Fuzhou (CN); Mingrui Chen, Fuzhou (CN); Liang Zhang, Changchun (CN); Fan Lv, Changchun (CN)

(73) Assignees: FUJIAN UNIVERSITY OF TECHNOLOGY, Fuzhou (CN); SHANDONG UNIVERSITY OF SCIENCE AND TECHNOLOGY, Qingdao (CN); FUZHOU UNIVERSITY, Fuzhou (CN)

( * ) Notice: Subject to any disclaimer, the term of this patent is extended or adjusted under 35 U.S.C. 154(b) by 380 days.

(21) Appl. No.: 18/409,775

(22) Filed: Jan. 10, 2024

(65) Prior Publication Data

US 2024/0280451 A1    Aug. 22, 2024

(30) Foreign Application Priority Data

Feb. 20, 2023    (CN) .......................... 202310135409.3

(51) Int. Cl.
*G01N 33/24* (2006.01)
*G01N 1/44* (2006.01)
*G01N 3/24* (2006.01)

(52) U.S. Cl.
CPC ................. *G01N 3/24* (2013.01); *G01N 1/44* (2013.01); *G01N 33/24* (2013.01); *G01N 2203/0048* (2013.01)

(58) Field of Classification Search
CPC ........... G01N 3/24; G01N 1/44; G01N 33/24; G01N 2203/0048
See application file for complete search history.

(56) References Cited

U.S. PATENT DOCUMENTS 11,474,013 B2 * 10/2022 Coe .......................... G01N 3/32

FOREIGN PATENT DOCUMENTS

| BR | 202021007459 U2 * | 10/2022 | |
| CN | 116754355 A * | 9/2023 | |
| CN | 116840074 A * | 10/2023 | ............... G01N 3/24 |

* cited by examiner

*Primary Examiner* — Jamel E Williams

(57) ABSTRACT

Disclosed are an underground engineering rock mass shear simulation test device, a test method and a test machine. The test method includes: setting different test conditions by a controller to perform cyclic shear test at high temperature, fracture shear seepage test, granite uniaxial compression test at high temperature and granite fracture shear test under constant normal stiffness boundary conditions at room temperature. The electric heating wire assembly, the fan assembly and the environmental box are combined to flexibly and uniformly heat the samples placed in the upper shear box and the lower shear box. In terms of shear-seepage test, this scheme proposes a second sample placing mechanism that realizes sealing through sealing capsule and sealing capsule pressing plate. It realizes stable sealing and facilitates monitoring and debugging of seepage parameters.

14 Claims, 10 Drawing Sheets

UNDERGROUND ENGINEERING ROCK MASS SHEAR SIMULATION TEST DEVICE, TEST METHOD AND TEST MACHINE THEREOF

CROSS-REFERENCE TO RELATED APPLICATIONS

This application is based upon and claims priority to Chinese Patent Application No. 202310135409.3, filed on Feb. 20, 2023, the entire contents of which are incorporated herein by reference.

TECHNICAL FIELD

The present disclosure relates to the technical field of rock mass mechanical information measurement. It relates in particular to an underground engineering rock mass shear simulation test device, a test method and a test machine.

BACKGROUND

Among the technical equipment of rock mass mechanics information measurement, there are many shear-seepage coupling test equipment and high temperature shear equipment, but most of them are only isolated single test equipment, that is, there are few equipment that can realize high temperature shear and shear seepage tests on one testing machine. Furthermore, there are some limitations in the current test equipment that can perform high temperature shearing, for example, the heating temperature of high temperature equipment is low (for example, Chinese patent CN110658085A, publication date: Jan. 7, 2020 and Chinese patent CN113109181A, publication date: Jul. 13, 2021, the maximum heating temperature recorded in the document is only 250° C., Chinese patent CN112284932A, publication date: Jan. 29, 2021, the maximum heating temperature recorded in the document is only 100° C.). It is clear that the temperature environment of the deeper rock mass cannot be reached. Therefore, further improvement of equipment is required to study the temperature environment of the deep rock mass.

In order to ensure the heating effect, the existing test equipment usually uses a heating rod placed in the shear box, which is easy to heat the sample unevenly (because there are only two heating directions). Moreover, the test device of the prior art has no thermal insulation equipment, and the real-time high temperature test and the cyclic heating test cannot be realized. For the sealing of experimental instruments, the shear seepage equipment of the prior art is usually sealed by smearing glue (such as Chinese patent CN112284932A, published on Jan. 29, 2021). However, the disadvantage is that the shear seepage box has poor sealing performance and the sealing rubber has a short service life. Moreover, the normal displacement of the sample is limited in the shear seepage process in the prior art, because the normal displacement will bring a high challenge to the sealing performance. Therefore, how to improve the operation convenience, test flexibility and reliability of the device so that it can perform reliable high temperature test and shear test to obtain accurate and effective results is a positive and practical issue.

SUMMARY OF THE DISCLOSURE

In view of this, it is an object of the present disclosure to propose an underground engineering rock mass shear simulation test device, a test method and a test machine which are reliable in implementation, convenient and flexible in operation and have good shear effects.

In order to achieve the above technical objectives, the technical solution adopted by the present disclosure is:

An underground engineering rock mass shear simulation test device, including:

a frame comprising a base and a gantry spanning over the base, wherein a test area is formed between a lower side of the gantry and the base;

an axial loading mechanism, which is set on a lower side of a middle part of the gantry, and is used to provide force loading for test samples in the test area;

a horizontal loading mechanism, which is arranged on both sides of the gantry close to the test area and is used for providing shear force loading to the test samples in the test area;

a first sample placing mechanism and a second sample placing mechanism, which are respectively arranged above the base and are used for placing test samples;

a linkage traction mechanism, which is arranged on the base and connected with the first sample placing mechanism and the second sample placing mechanism respectively, and used for driving the first sample placing mechanism or the second sample placing mechanism to move into or out of the test area;

a controller, which is connected with the axial loading mechanism, the horizontal loading mechanism and the linkage traction mechanism respectively, and controls the axial loading mechanism, the horizontal loading mechanism and the linkage traction mechanism to start or stop;

wherein the horizontal loading mechanism and the axial loading mechanism have a first matching state and a second matching state with the first sample placing mechanism or the second sample placing mechanism;

in the first matching state, the first sample placing mechanism or the second sample placing mechanism is located in the test area, the axial loading mechanism loads an axial force to the sample in the first sample placing mechanism or the second sample placing mechanism, and the horizontal loading mechanism loads a shear force to the sample in the first sample placing mechanism or the second sample placing mechanism;

in the second matching state, the axial loading mechanism and the horizontal loading mechanism relieve the force loading applied to the first sample placing mechanism or the second sample placing mechanism.

An underground engineering rock mass shear simulation test method, comprising the underground engineering rock mass shear simulation test device above mentioned, used for performing cyclic shear test at high temperature, fracture shear seepage test, granite uniaxial compression test at high temperature and/or granite fracture shear test;

the underground engineering rock mass shear simulation test method test method including:

setting constant normal load boundary conditions and constant normal stiffness boundary conditions at room temperature by the controller;

performing cyclic shear test at high temperature and fracture shear seepage test under constant normal load boundary conditions; a heating temperature of the cyclic shear test at high temperature is room temperature –400° C. with a precision of ±2° C. and a heating rate of 5° C./h-400° C./h;

performing granite fracture shear tests under constant normal stiffness boundary conditions at room temperature.

A testing machine, which implements the underground engineering rock mass shear simulation test method mentioned above, for performing cyclic shear test at high temperature, fracture shear seepage test, granite uniaxial compression test at high temperature and/or granite fracture shear test.

BRIEF DESCRIPTION OF THE DRAWINGS

In order to explain more clearly the embodiments of the present disclosure or the technical solution in the prior art, the following will briefly introduce the drawings to be used in the embodiments or the prior art description. Obviously, the drawings in the following description are only some embodiments of the present disclosure. For those skilled in the art, other drawings can be obtained according to these drawings without creative labor.

DETAILED DESCRIPTION OF THE EMBODIMENTS

Figure 1:
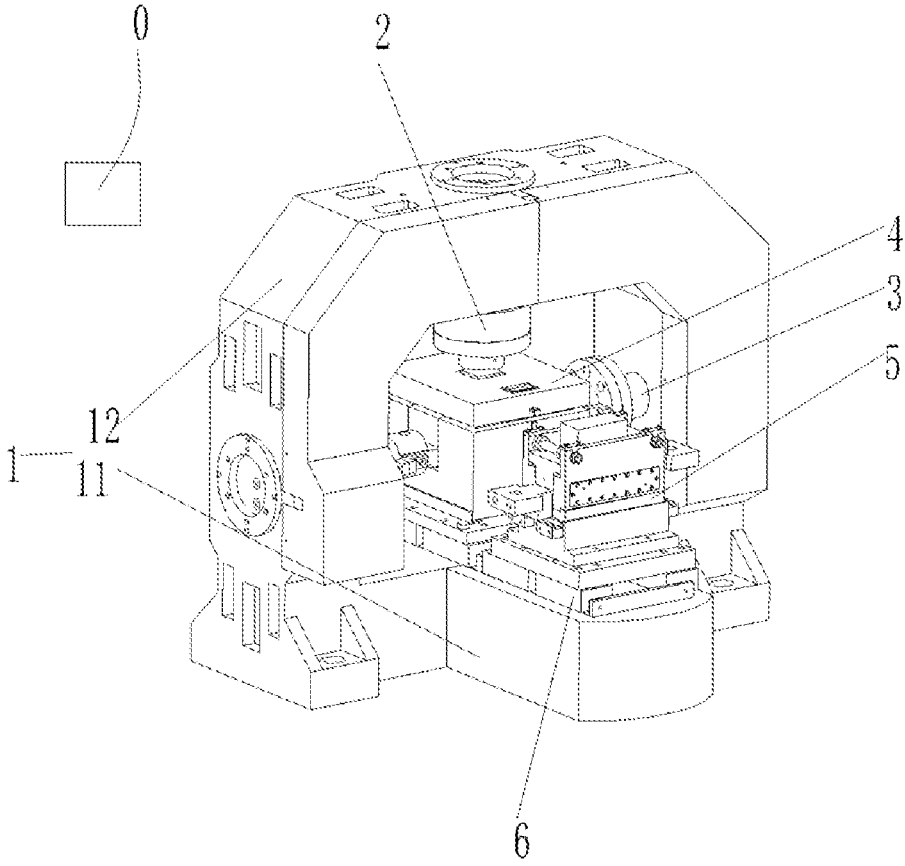
FIG. 1 is one of the schematic diagrams of a brief embodiment of the present disclosure, showing a state in which the first sample placing mechanism is located in the test area.

The present disclosure will be further described in detail with reference to the drawings and embodiments.

Embodiment 1

As shown in one of FIGS. 1 to 12, the present embodiment provides an underground engineering rock mass shear simulation test device, which includes a controller 0, a frame 1, an axial loading mechanism 2, a horizontal loading mechanism 3, a first sample placing mechanism 4, a second sample placing mechanism 5 and a linkage traction mechanism 6.

The frame 1 includes a base 11 and a gantry 12 spanning over the base 11, wherein a test area 13 is formed between the lower side of the gantry 12 and the base 11.

The axial loading mechanism 2 is arranged on the lower side of the middle part of the gantry 12 and is used for providing force loading for the test in the test area 13.

The horizontal loading mechanism 3 is arranged on both sides of the gantry 12 close to the test area 13, and is used for providing shear force loading to a sample in the test area 13.

The first sample placing mechanism 4 and the second sample placing mechanism 5 are respectively arranged above the base 11 and are used for placing the samples.

The linkage traction mechanism 6, which is arranged on the base 11 and is connected to the first sample placing mechanism 4 and the second sample placing mechanism 5 respectively, and is used for driving the first sample placing mechanism 4 or the second sample placing mechanism 5 to move into or out of the test area 13.

The controller 0 is connected with the axial loading mechanism 2, the horizontal loading mechanism 3 and the linkage traction mechanism 6 respectively, and controls the axial loading mechanism, the horizontal loading mechanism and the linkage traction mechanism to start or stop.

As for the controller 0, the controller 0 in this scheme can adopt the EDC full-digital servo controller imported from DOLI of Germany. This kind of measurement and control device has multiple measurement channels, which can perform closed-loop control on any one of the channels, and can perform impact free conversion on the control channel in the test. The measurement and control device has the advantages of convenient operation, strong fault tolerance, accurate measurement, complete protection function and high control accuracy. The controller 0 can work independently or under the control of computer.

The horizontal loading mechanism 3 and the axial loading mechanism 2 have a first matching state and a second matching state with the first sample placing mechanism 4 or the second sample placing mechanism 5.

In a first matching state, the first sample placing mechanism 4 or the second sample placing mechanism 5 is located in the test area 13, the axial loading mechanism 2 loads an axial force to the sample in the first sample placing mechanism 4 or the second sample placing mechanism 5, and the horizontal loading mechanism 3 loads a shear force to the sample in the first sample placing mechanism 4 or the second sample placing mechanism 5.

In the second matching state, the axial loading mechanism 2 and the horizontal loading mechanism 3 relieve the force loading applied to the first sample placing mechanism 4 or the second sample placing mechanism 5.

In this embodiment, the axial loading mechanism 2 includes an axial oil cylinder 21, which is mounted by means of a mounting member on a lower side of the middle part of the gantry 12, the driving end of the axial oil cylinder 21 being vertically downward facing the sample located in the test area 13, the axial oil cylinder 21 being connected to the controller 0 and controlled by the controller 0 to start or stop the operation.

Figure 2:
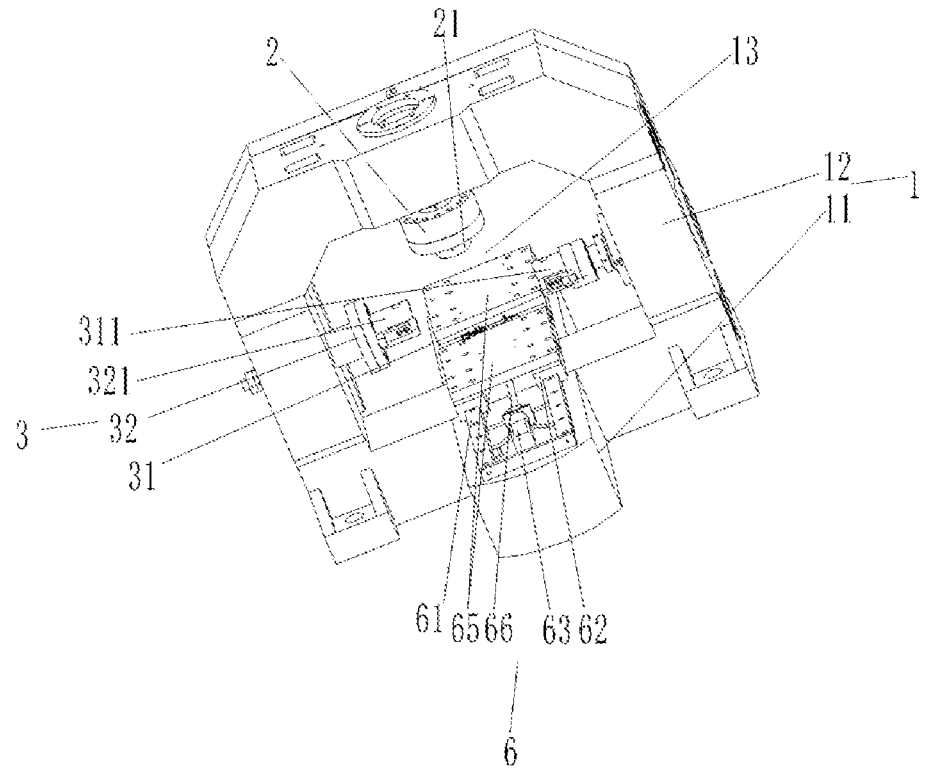
FIG. 2 is a schematic diagram schematically illustrating a part of the structure of the present disclosure, wherein the first and second sample placing mechanisms are hidden.
Figure 3:
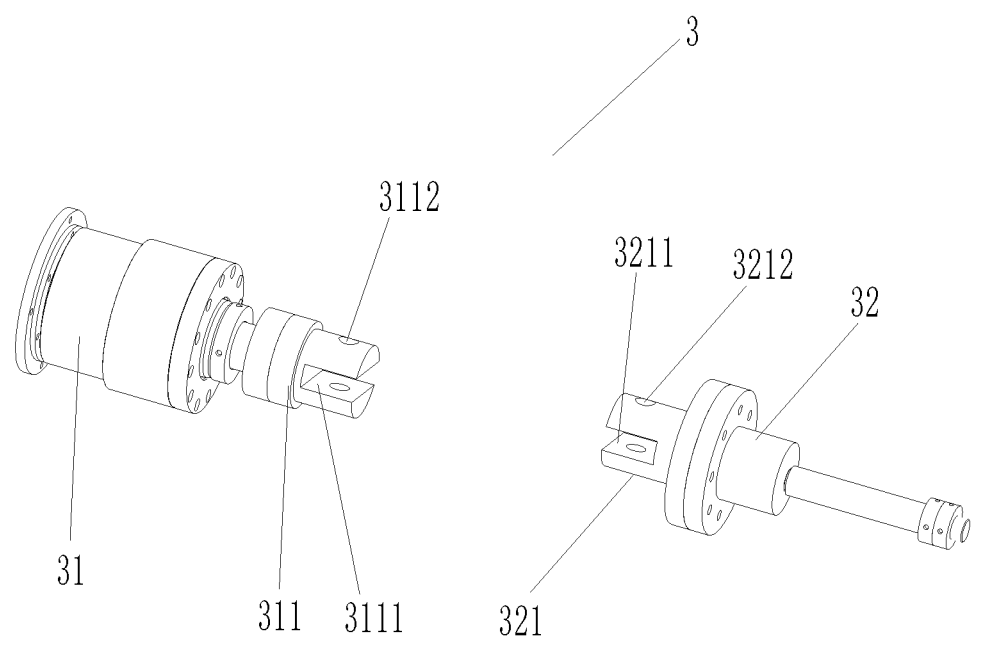
FIG. 3 is a schematic diagram of a brief embodiment of the horizontal loading mechanism of the present disclosure.
Figure 4:
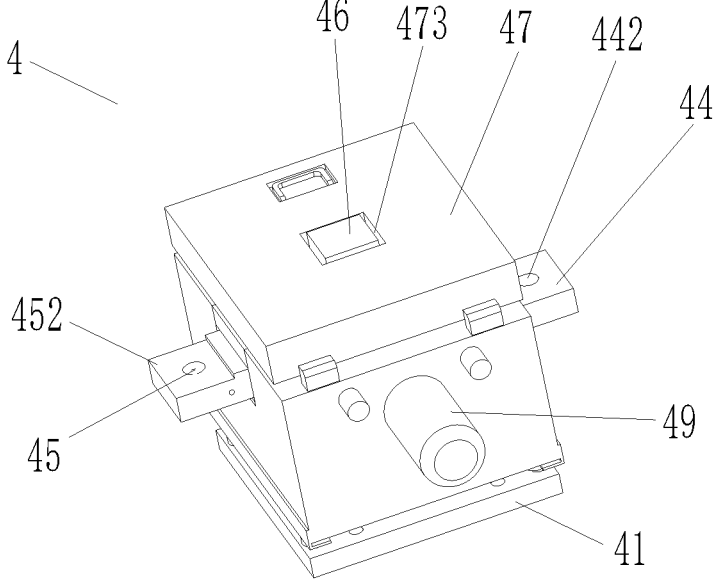
FIG. 4 is a schematic diagram of a brief embodiment of the first sample placing mechanism of the present disclosure.
Figure 5:
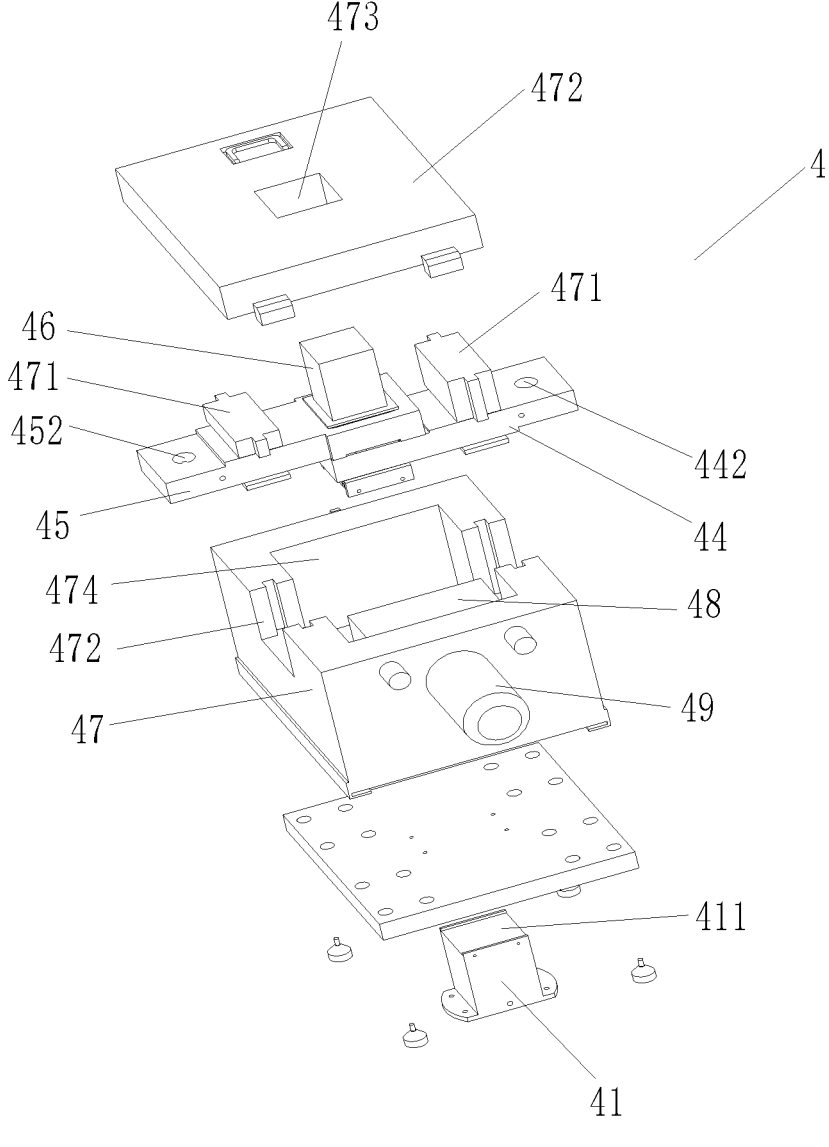
FIG. 5 is a schematic exploded view of a structure of the first sample placing mechanism of the present disclosure.
Figure 6:
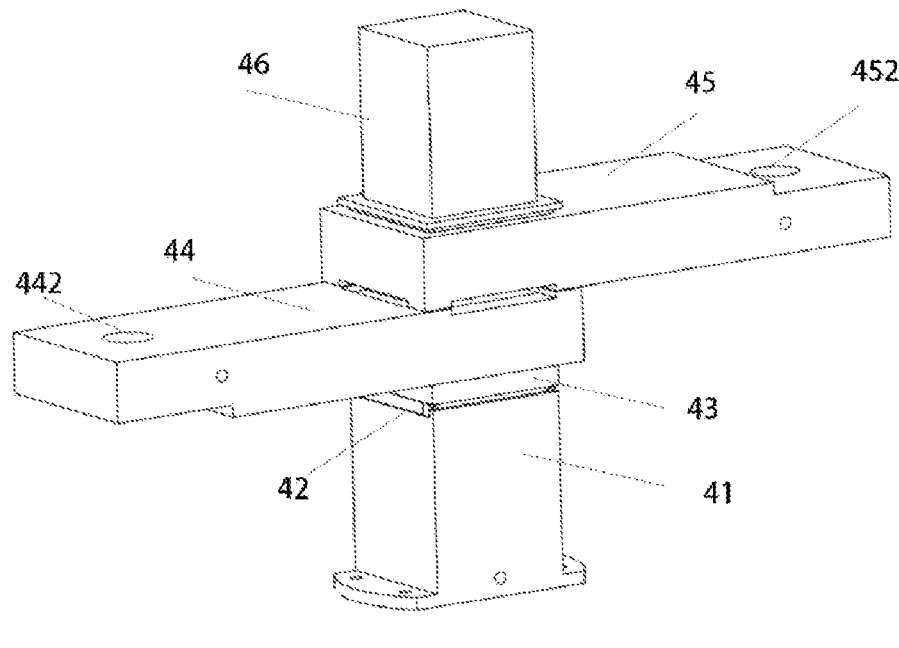
FIG. 6 is a schematic embodiment of the first sample placing mechanism of the present disclosure without an environmental box.
Figure 7:
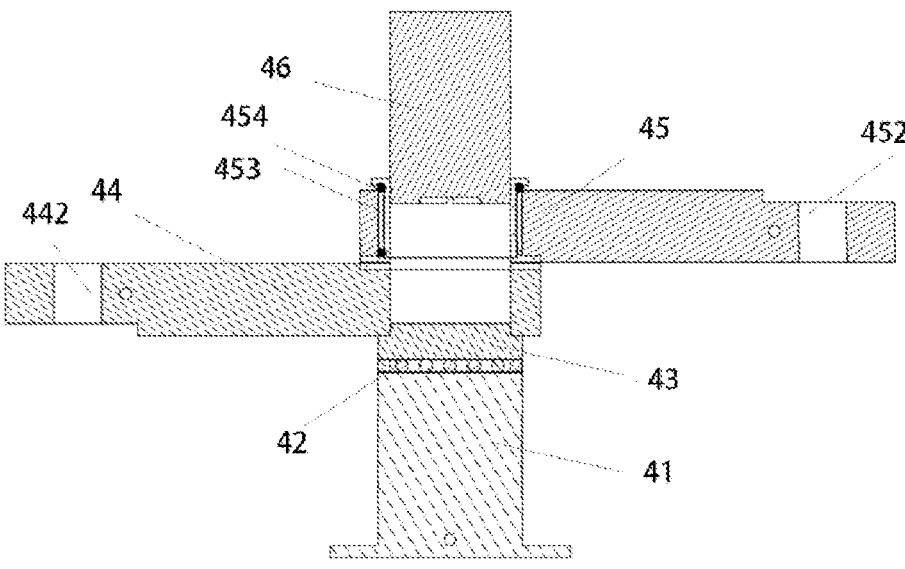
FIG. 7 is a schematic cross-sectional view of the embodiment shown in FIG. 6.
Figure 8:
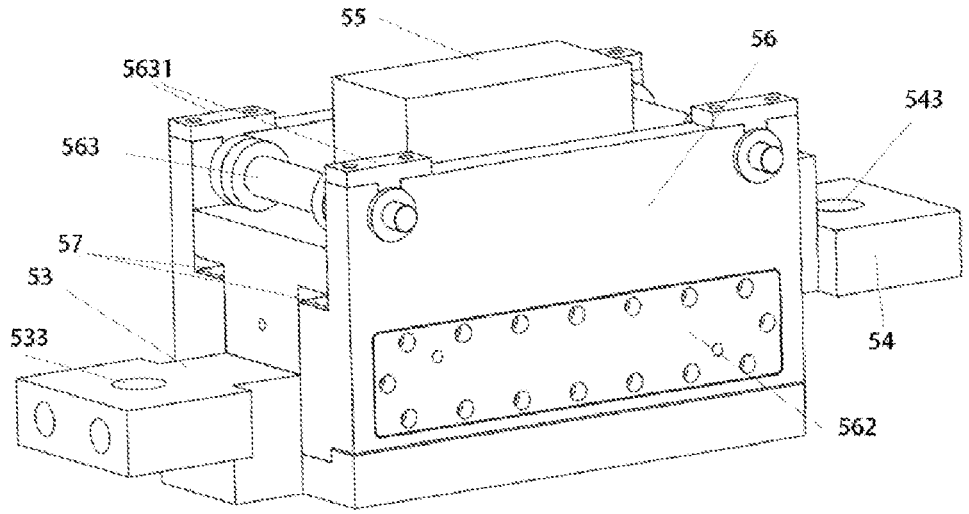
FIG. 8 is a schematic diagram of a brief embodiment of the second sample placing mechanism of the present disclosure.
Figure 9:
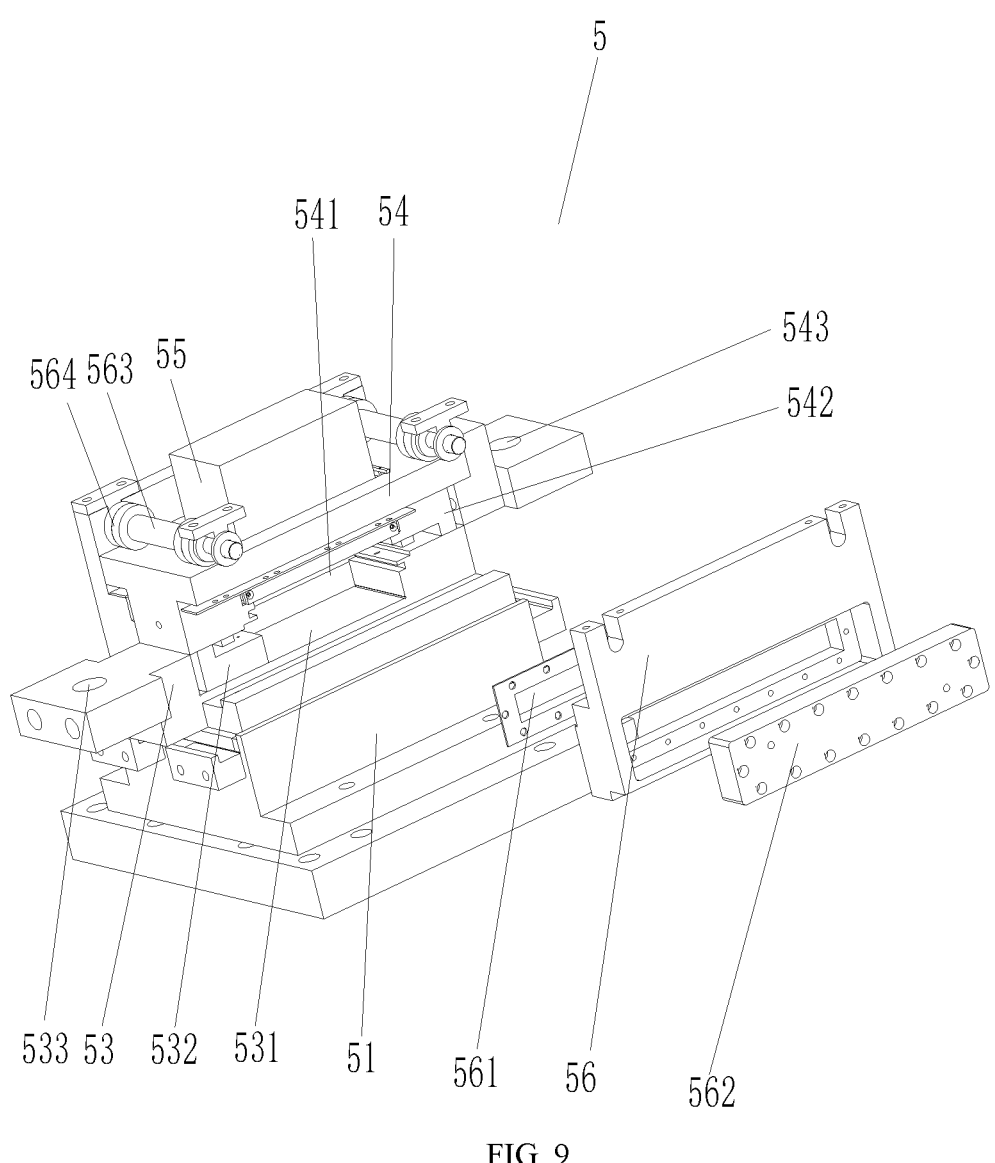
FIG. 9 is a schematic partial exploded view of a structure of the second sample placing mechanism of the present disclosure.
Figure 10:
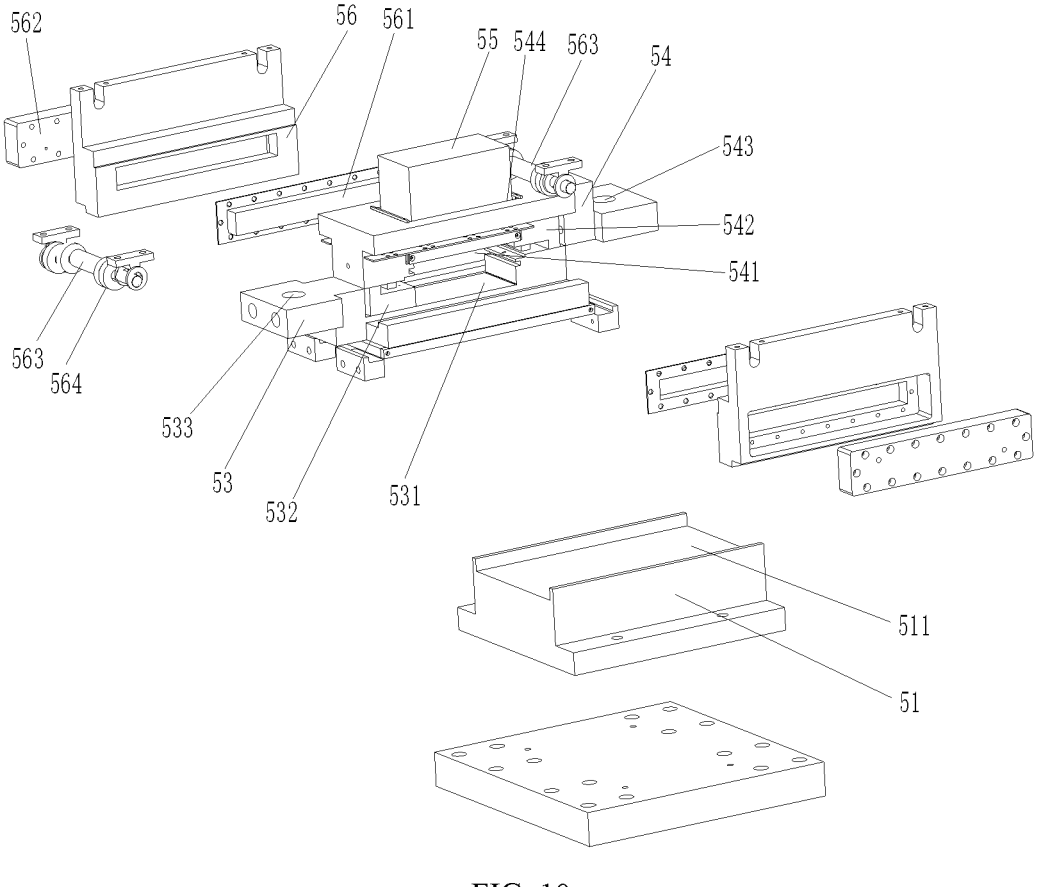
FIG. 10 is a schematic exploded view of a structure of the second sample placing mechanism of the present disclosure.
Figure 11:
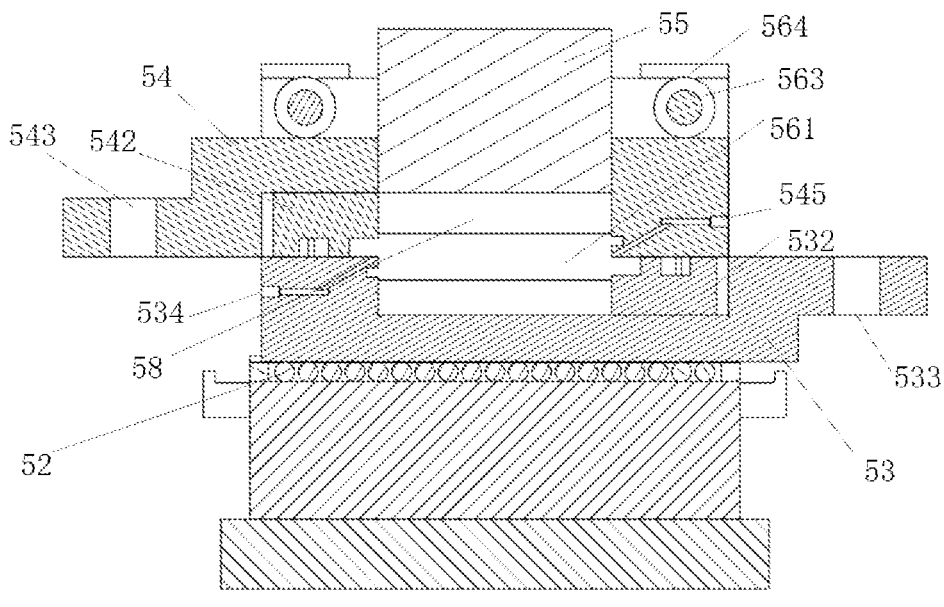
FIG. 11 is a schematic cross-sectional view of a second sample placing mechanism of the present disclosure.

On the basis of FIGS. 1 to 12, with particular reference to one of FIGS. 1 to 3, as a preferred alternative embodiment, the horizontal loading mechanism 3 in the present solution includes a horizontal shear oil cylinder 31 and a reaction force device 32.

The horizontal shear oil cylinder 31, which is arranged on the side of the gantry 12 close to the test area 13, the driving end thereof faces the test area 13 and is used for cooperating with the side of the sample located in the test area 13 and for providing horizontal shear force loading, the horizontal shear oil cylinder 31 is connected to a controller and is controlled by the controller 0 to start or stop the operation.

The reaction force device 32 is arranged on the other side of the gantry 12 near the test area 13 and is used for mating connection with the other side of the sample located in the test area 13.

Figure 12:
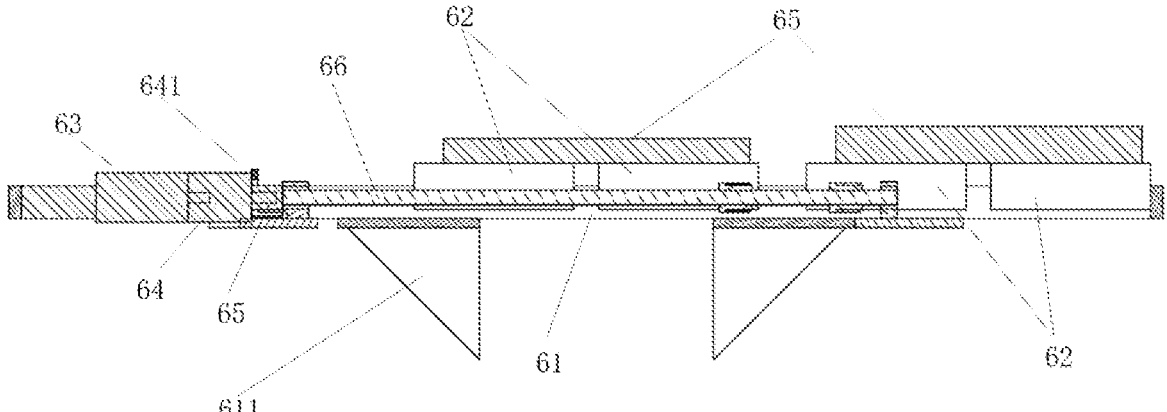
FIG. 12 is a schematic diagram of a brief implementation structure of the linkage traction mechanism of the present disclosure.

On the basis of FIGS. 1 to 12 and in combination with FIG. 2 or 12, the linkage traction mechanism 6 in this scheme includes a linear guide rail 61, a pair of sliding block 62, a servo motor 63, and a speed reducer 64.

The linear guide rail 61 is mounted on the base 11 by means of a support block 611, and both ends of the linear guide rail 61 span the test area 13 below the gantry 12, the support block 611 being used for improving the structural stability and strength of the linear guide rail 61.

The pair of sliding block 62 is slidably connected to the linear guide rail 61, wherein the upper end of each sliding block 62 is connected with a base plate assembly 65, and the base plate assembly 65 is cooperatively connected with the first sample placing mechanism 4 or the second sample placing mechanism 5.

The servo motor 63 fixedly connected to one end of the linear guide rail 61, the driving end thereof facing the other end of the linear guide rail 61, the servo motor 63 being connected to the controller 0 and controlled by the controller 0 to start or stop the operation.

The power input end of the speed reducer 64 is connected to the driving end of the servo motor 63, and the power output end of the speed reducer 64 is connected to a screw rod 66 through a coupling. The end of the screw rod 66 away from the speed reducer 64 extends to the other end of the linear guide rail 61, and the speed reducer 64 is also provided with a speed reducer bracket 641 for auxiliary fixing.

The lower ends of the pair of sliding block 62 are fixedly connected with threaded connection blocks connected to the screw rod 66. The screw rod 66 is driven by the servo motor 63 to rotate, so that the pair of sliding block 62 drives the first sample placing mechanism 4 and the second sample placing mechanism 5 to synchronously translate along the length direction of the linear guide rail 61, so that the first sample placing mechanism 4 or the second sample placing mechanism 5 move into or out of the test area 13 under the gantry 12.

Focusing on one of FIGS. 4 to 7, as an alternative embodiment, the first sample placing mechanism 4 described in the present solution includes a first foundation 41, a first roller rows 42, a first base plate 43, a lower shear box 44, an upper shear box 45, a first pressure head 46, an environmental box 47, an electric heating wire assembly 48, and a fan assembly 49.

The lower part of the first foundation 41 is connected to a base plate assembly 65 on one of the sliding block 62.

The first roller rows 42 movably disposed on an upper end surface of the first foundation 41, the first foundation 41 being provided with a first recess 411 for accommodating the first roller rows 42, the upper side of the first roller rows 42 being flush with or higher than the upper end of the first recess 411.

The first base plate 43 which is disposed above the first foundation 41 and whose lower end surface is in contact with the upper side of the first roller rows 42.

The lower shear box 44, one end of which is disposed on an upper end surface of the first base plate 43, and one end of the lower shear box 44 is further provided with a first sample accommodating slot 441 through the upper and lower end surfaces thereof, the structure outline of the first sample accommodating slot 441 being adapted to a lower part of the sample, and the upper end surface of the first base plate 43 being provided with a convex structure adapted to the lower structure of the first sample accommodating slot 441 of the lower shear box 44, by means of which, when the lower shear box 44 is moved, the first base plate 43 can be driven to move, and since the first base plate 43 is in contact with the first roller rows 42, the relative friction force for the movement of the lower shear box 44 can be reduced. The other end of the lower shear box 44 is provided with a first mounting through hole 442 for cooperating with the horizontal shear oil cylinder 31, the horizontal shear oil cylinder 31 is connected with a first connecting block 311, the first connecting block 311 is provided with a first U-shaped groove 3111 for engaging and cooperating with the other end of the lower shear box 44, and the first U-shaped groove 3111 is provided with a first consistent perforation 3112 adapted to and cooperating with the structure of the first mounting through hole 442. The other end of the lower shear box 44 is clamped with the first U-shaped groove 3111, and a pin passes through the first through hole 3112 and the first mounting through hole 442, so that the other end of the lower shear box 44 is detachably and fixedly connected with the first connecting block 311.

The upper shear box 45, one end of which is placed on an upper end surface of one end of the lower shear box 44, one end of the upper shear box 45 is provided with a second sample accommodating slot 451 through the upper and lower end surfaces thereof, and the structure outline of the second sample accommodating slot 451 is adapted to the upper part of the sample; The other end of the upper shear box 45 is provided with a second mounting through hole 452 for cooperating with the reaction force device 32, the reaction force device 32 is connected with a second connecting block 321, the second connecting block 321 is provided with a second U-shaped groove 3211 for engaging with the other end of the upper shear box 45, and the second U-shaped groove 3211 is provided with a second through hole 3212 adapted to and cooperating with the structure of the second mounting through hole 452, After the other end of the upper shear box 45 is clamped with the second U-shaped groove 3211, a pin passes through the second through hole 3212 and the second mounting through hole 452, so that the other end of the upper shear box 45 is detachably and fixedly connected with the second connecting block 321. In order to reduce the friction between the upper and lower shear boxes, as an example, an aperture is provided between the upper and lower shear boxes, so that four grooves are provided around the first sample accommodating slot 441 of the lower shear box 44, balls are placed inside to reduce friction between upper and lower shear boxes during shearing. In order to avoid large friction between the upper part of the sample and the second sample accommodating slot 451 of the upper shear box 45 in case of shear fracture of the sample in the shear test, in this scheme, the upper part of the sample is also sleeved with a connecting sleeve 453, and a third roller rows 454 is also provided between the connecting sleeve 453 and the second sample accommodating slot 451.

The first pressure head 46, the lower end of which is movably inserted into a second sample accommodating slot 451 of the upper shear box 45 and cooperates with the first base plate 43 to constrain and fix the sample in the first sample accommodating slot 441 and the second sample accommodating slot 451; The upper end of the first pressure head 46 is adapted to cooperate with the drive end of the axial oil cylinder 21.

The environmental box 47 is a detachable box structure, forming a accommodating cavity 474 inside, and one end of the lower shear box 44 and the upper shear box 45 are received in the accommodating cavity 474, the two sides of the environmental box 47 face the upper shear box 45 and the lower shear box 44 respectively, the upper end of the environmental box 47 is provided with an avoiding through hole 473 for passing through the other end of the first pressure head 46.

The electric heating wire assembly 48 is arranged in the accommodation cavity 474 and is connected to the controller 0 and controlled by the controller 0 to start or stop.

The fan assembly 49 is disposed on one side of the environmental box 47, and the wind output end of the environmental box 47 corresponding to the fan assembly 49 is provided with an air duct connected to the accommodation cavity 474 of the environmental box 47, and the fan assembly 49 is used for guiding and blowing the air heated by the electric heating wire assembly 48 to the surface of the sample, so as to realize the temperature regulation of the sample.

Wherein the first pressure head 46 and the lower shear box 44 are uniformly provided with more than one displacement sensors, and the upper shear box 45, the lower shear box 44 and the bottom of the first pressure head 46 are all provided with a reserved hole for threading temperature sensors to the surface of the sample.

Focusing on the combination of FIGS. 8 to 11, as an alternative embodiment, the second sample placing mechanism 5 described in the present solution includes a second foundation 51, a second roller row 52, a lower shear seepage box 53, an upper shear seepage box 54, a pair of side plates 56 and a second pressure head 55.

The lower part of the second foundation 51 is connected to a base plate assembly 65 on another sliding block 62.

The second roller rows 52 movably disposed on an upper end surface of a second foundation 51, the upper end surface of the second foundation 51 being provided with a second sink for accommodating the second roller rows 52, the upper side of the second roller rows 52 being flush with or higher than the upper end of the second sink.

The lower shear seepage box 53, one end of which is placed on an upper end surface of the second foundation 51, a lower end surface of one end of the lower shear seepage box 53 being fitted with a second roller rows 52, a third sample accommodating slot 531 being an open U-shaped slot on both sides, and a first cushion block 532 being arranged on the other end of the lower shear seepage box 53, The upper end surface of the first cushion block 532 is flush with the upper end surface of the lower shear seepage box 53; the other end of the lower shear seepage box 53 is provided with a third mounting through hole 533 and is used for cooperating with the horizontal shear oil cylinder 31.

When the horizontal shear oil cylinder 31 cooperates with the lower shear seepage box 53, a pin passes through the first through hole 3112 and the third mounting through hole 533, so that the other end of the lower shear seepage box 53 is detachably and fixedly connected with the first connecting block 311.

The upper shear seepage box 54, one end of which is placed on an upper end surface of one end of the lower shear seepage box 44 and a lower end surface of one end thereof is in contact with an upper end surface of the first cushion block 532, a lower end surface of one end of the upper shear seepage box 54 is provided with a fourth sample accommodating slot 541, which is U-shaped slot open on both sides, and one side of the fourth sample accommodating slot 541 away from the other end of the upper shear seepage box 54 is provided with a second cushion block 542, the lower end surface of the second cushion block 542 is flush with the lower end surface of the upper shear seepage box 54, the upper end surface of one end of the lower shear seepage box 53 is in contact with the lower end surface of the second cushion block 542; the other end of the upper shear seepage box 54 is provided with a fourth mounting through hole 543 and is used for cooperating with the reaction force device 32. When the reaction force device 32 cooperates with the upper shear seepage box 54, a pin passes through the second through hole 3212 and the fourth mounting through hole 543, so that the other end of the upper shear seepage box 54 is detachably and fixedly connected with the second connecting block 321.

The pair of side plates 56 are arranged oppositely on both sides of the upper shear seepage box 54 and the lower shear seepage box 53, so that the upper shear seepage box 54 and the lower shear seepage box 53 are movably constrained between the pair of side plates 56 (a slide rail 57 may be mounted on the side plate, and the upper shear seepage box 54 is placed on the slide rail 57 for reducing friction between the upper and lower shear seepage boxes), wherein the third sample accommodating slots 531, the fourth sample accommodating slot 541, the first cushion block 532. The accommodating area 58 for accommodating a sample is formed between the second cushion block 542. Sealing capsules 561 are provided on both sides of the accommodating area 58. Sealing grooves are provided on the end surfaces of the first cushion block 532 and the upper shear seepage box 54 and the end surfaces of the second cushion block 542 and the lower shear seepage box 53, and sealing strips are embedded in the sealing grooves. In addition, one end of the upper shear seepage box 54 is provided with a water inlet 545 penetrating into the accommodating area 58. The lower shear seepage box 53 is further provided with a water outlet 534 at one end penetrating into the accommodating area 58. The upper ends of the pair of side plates 56 are detachably connected to a pair of oppositely arranged pressing roller shafts 563, both ends of the pressing roller shafts 563 are rotatably connected to the pair of side plates 56, and the pressing roller shafts 563 are sleeved with an annular pressing roller block 564 for cooperating with the upper end surface of the upper shear seepage box 54. A pair of the side plates 56 is further provided with a sealing capsule pressing plate 562 cooperating with the sealing capsule 561 corresponding to the sealing capsule 561.

The second pressure head 55, the lower end of which movably penetrates into the fourth sample accommodating slot 541 of an upper shear seepage box 54 against a sample placed in a housing cavity 474, the upper end of the upper shear seepage box 54 being provided with an avoiding slot 544 for the second pressure head 55 to penetrate, and the upper end of the second pressure head 55 being used for mating with the drive end of the axial oil cylinder 21.

In the present solution, the end of the lower shear seepage box 53 may also be slotted to place a special sealing rubber block; Meanwhile, a cushion block is placed at the ends of the upper shear seepage box 54 and the lower shear seepage box 53, which can facilitate fine adjustment, adjust the position of the sample to adapt, and increase the tightness of the shear process.

As an embodiment, the upper shear seepage box 54 and the lower shear seepage box 53 side plates are connected by two pressing roller shafts 563, and the two ends are fastened by nuts; the pressing roller block 564 is connected to the side plate by screws to fix the pressing roller shaft; Place the sealing capsule 561 in the side plate and fasten it with the sealing capsule pressing plate 562; a second pressure head 55 is placed on the upper shear seepage box 54 and compacted by the axial oil cylinder 21 to achieve a shear seepage seal.

The second pressure head 55 and the lower shear seepage box 53 are uniformly provided with more than one displacement sensor.

In the present embodiment, the axial loading mechanism 2 may cooperate with a controller in combination with a sensor group to form an axial loading system. By using a linear hydraulic cylinder loading mode and cooperating with corresponding feedback sensors (such as a pressure sensor and a displacement sensor), the load value in the axial loading and the displacement value of the cylinder movement are measured, and the measured load value and the displacement value are fed back to the data acquisition control system or the controller, then the hydraulic cylinder closed loop control is performed.

As an embodiment, the axial loading system includes: an axial loading mechanism, an axial force sensor, an axial displacement sensor, an axial loading EDC monitor, an axial loading servo valve, and the like. The axial force sensor is used for detecting a load value loaded by the axial force. The axial displacement sensor is used for detecting the displacement value of the oil cylinder movement. The axial loading EDC measuring and controlling device is used for receiving the load value loaded by the axial force and the displacement value of the cylinder movement for closed-loop control of the hydraulic cylinder. The axial loading servo valve is used for controlling the oil pressure and flow of the hydraulic cylinder during axial loading.

The horizontal loading mechanism 3 can cooperate with the controller and the sensor group to form a horizontal loading system. By adopting a linear hydraulic cylinder loading mode, the load value detected in the horizontal shear loading and the displacement value of the cylinder movement are fed back to the data acquisition control system or the controller for closed-loop control of the hydraulic cylinder.

As an embodiment, the horizontal loading system includes: a shear loading mechanism (horizontal loading mechanism), a shear force sensor, a shear displacement sensor, a shear loading EDC monitor, and a shear loading servo valve. The shear force sensor is used for detecting a load value loaded in shearing; the shear displacement sensor is used for detecting the displacement value of the oil cylinder movement during shearing. The shear loading EDC measurement and control device is used for receiving a load value loaded by the shear force and a displacement value of the cylinder movement for closed-loop control of the hydraulic cylinder. The shear loading servo valve is used for controlling the oil pressure and flow of the hydraulic cylinder during shear loading.

The upper shear seepage box 54, the lower shear seepage box 53, the second foundation 51, the second roller rows 52, a pair of side plates 56 and the first cushion block 532, the second cushion block 542, the sealing capsule 561 and other sealing elements and connection assemblies can form a seepage control system in combination with an external device for injecting seepage media, a flow monitoring unit and a control unit, etc., and the upper and lower shear seepage boxes 53 are placed into the second roller rows 52 of the shear seepage base (the second foundation 51), the shear seepage box (second sample placing mechanism 5) is transported to the test position by the linkage traction mechanism 6 for test; The shear seepage box includes an upper shear seepage box 54 and a lower shear seepage box 53. Inject the seepage medium from the water inlet of the upper shear seepage box 54, measure the water volume at the water outlet of the lower shear seepage box 53, and calculate the flow rate until the stable seepage flow is reached. The seepage control system records the normal load, the shear load, the shear displacement and the normal displacement in the shear process in real time by means of the seepage pressure, the normal load, the normal stiffness and the shear rate set by the data acquisition control system or the controller, so as to complete the shear seepage test.

The environmental box 47, the electric heating wire assembly 48, the fan assembly 49 and the controller, in combination with the sensor group, can form a high temperature system, the high temperature system heats a sample in the form of an environmental box 47, and the temperature can reach 400° C. The environmental box 47 includes a cover plate at the top, left and right insert plates and a bottom plate arranged at both sides.

In one embodiment, the outer wall of the environmental box 47 is formed by a stainless steel plate, the inner wall of the environmental box 47 is attached with a thermal insulation cotton, the interior of the environmental box 47 is heated by a heating wire, the external of the environmental box 47 is equipped with a control meter to control the power of the heating wire for heating, and a fan (fan assembly 49) is used to blow the heat flow, and a louver is provided above the thermal insulation plate for adjusting the wind direction to heat the environmental box 47 evenly.

In the present embodiment, the sample is heated in the form of an environmental box 47. The outer wall of the environmental box 47 is formed of stainless steel plates, and the inner wall is attached with a heat insulation cotton. The interior is heated by a heating wire. An electric meter is configured outside the environmental box 47 to control the power of the heating wire for heating. The heat is blown by a fan. The wind direction can be further adjusted by an auxiliary component to heat the environmental box evenly.

In the present solution, the horizontal shear oil cylinder 31 and the axial oil cylinder 21 are controlled by a hydraulic system, and the hydraulic system detects and controls the hydraulic pump station in real time.

In terms of monitoring and measurement, both the horizontal shear loading system and the axial loading system can adopt the linear hydraulic cylinder loading mode. The controller 0 adopts the high-precision digital controller EDCI 20 and is equipped with the corresponding measuring board card. The load value is measured by the load sensor, and the displacement, force and displacement measured by the displacement sensor are fed back to the EDC controller, forming a closed-loop control system to realize accurate control.

The piston displacement of the hydraulic cylinder is measured by the magnetic displacement sensor. The force sensor used in the present disclosure is a spoke sensor, and the sensor has a large rigidity, and the sensor temperature compensation technology can be further used, thereby ensuring the stability and reliability of long-term continuous measurement. Deformation sensors are set at four corners of the pressure head to monitor the normal displacement of the sample in real time. The space for temperature sensor can be reserved at the first and second pressure heads, and holes are opened on the side wall of the shear box, so that the temperature sensor can be placed on the sample, and the temperature of the sample in three directions can be obtained in real time.

With the above technical solution, the present disclosure has the following beneficial effects compared with the prior art:

In the present solution, a first sample placing mechanism 4 capable of controlling the temperature is proposed to solve the problems in the prior art that it is difficult to heat the samples and the temperature span is small. The first sample placing mechanism 4 combines an electric heating wire assembly, a fan assembly and an environmental box to flexibly and uniformly heat the samples placed on the upper shear box 45 and the lower shear box 44; In terms of shear-seepage test, this scheme proposes a second sample placing mechanism 5 for sealing through sealing capsule and sealing capsule pressing plate. Meanwhile, combined with the cushion blocks and sealing strips matched in the upper shear seepage box and the lower shear seepage box, it realizes stable sealing and facilitates monitoring and commissioning of seepage parameters. Some parts of the equipment provided in this scheme are made of materials with high elasticity and certain hardness, with long service life. In addition, the equipment is allowed to have horizontal and normal displacement on the fracture surface during the test.

In addition, the present disclosure has the following advantages:

(1) In this scheme, the axial loading mechanism and the horizontal loading mechanism can provide sufficient rigidity and stable and reliable normal and shear servo control by combining the servo drive.

(2) In this scheme, the first sample placing mechanism heats the samples by means of electric heating wire assembly, and can also realize high temperature gas guidance by adding louver and other auxiliary guide elements, so that the heating is more uniform, and the maximum heating temperature can reach 400° C. On this basis, multi-level heating rate can be set as required, and the physical and mechanical properties of rock under slow temperature rise and thermal shock can be studied.

(3) In this scheme, the first sample placing mechanism and the second sample placing mechanism are moved by the linkage traction mechanism, which are convenient and stable. The linkage traction mechanism adopts the cooperation of servo motor, reducer, reducer support, coupling, lead screw and linear guide rail, which can improve the translation stability and accuracy of the sample placing mechanism.

(4) The device and test method of the present disclosure are mainly used for uniaxial and biaxial loading and shear tests of rock or concrete, uniaxial and biaxial loading tests at high temperature can also be carried out by equipping components such as an environmental box. The equipment is characterized by large rigidity of main machine, accurate measurement, high control accuracy and good long-term stability. It can be expanded and upgraded to realize dynamic load and true triaxial loading test in the later period.

Embodiment 2

Based on the above embodiment 1, the present embodiment provides an underground engineering rock mass shear simulation test method, comprising an underground engineering rock mass shear simulation test device as described in embodiment 1, which is used for performing cyclic shear test at high temperature, fracture shear seepage test, granite uniaxial compression test at high temperature and/or granite fracture shear test. In the test method, constant normal load boundary conditions and constant normal stiffness boundary conditions at room temperature are set by the controller.

cyclic shear test at high temperature and fracture shear seepage test are carried out under the condition of constant normal load boundary. The heating temperature of cyclic shear test at high temperature is room temperature –400° C., the precision of the heating temperature of cyclic shear test at high temperature is ±2° C., and the heating rate of the heating temperature of cyclic shear test at high temperature is 5° C./h-400° C./h.

The room temperature in this disclosure is ambient temperature, in general, the room temperature is 25° C.

Granite fracture shear tests were carried out under constant normal stiffness boundary conditions at room temperature.

Embodiment 3

In combination with one of FIGS. 1 to 12, as an optional embodiment of Embodiment 2, the embodiment provides a cyclic shear test scheme under constant normal load boundary conditions at high temperature, wherein the heating temperature of the cyclic shear test at high temperature is room temperature-400° C., the accuracy of the heating temperature of the cyclic shear test at high temperature is ±2° C., and the heating rate of the heating temperature of the cyclic shear test at high temperature is 5° C./h-400° C./h. It includes the following steps:

S1, placing the first foundation 41 and the environmental box 47 of the first sample placing mechanism 4 on the base plate assembly 65 on one of the sliding block 62 of the linkage traction mechanism 6, partially disassembling the environmental box 47 so that its interior is opened, and successively placing the first roller rows 42, the first base plate 43 and the lower shear box 44 on the end of the first foundation 41 in the accommodation cavity 474;

S2, placing the lower part of the rock sample into the first sample accommodating slot 441 of the lower shear box 44;

S3, placing the upper shear box 45 above the lower shear box 44 so that the upper part of the sample is placed in the second sample accommodating slot 451 of the upper shear box 45, placing the temperature sensor from the reserved holes of the upper shear box 45, the lower shear box 44 and the first pressure head 46 to the upper surface of the sample (the temperature sensor of the upper surface passes through the reserved hole of the first pressure head 46), the front surface and the left surface, and fixing the temperature sensor in the reserved holes with asbestos, wherein: the temperature sensor is also provided inside the environmental box and is used for feedback and assisting in controlling the temperature in the environmental box;

S4, assembling the disassembled part of the environmental box 47, and placing a first pressure head 46 at a position of the avoiding through hole 473 above the environmental box 47 so that the lower end of the first pressure head 46 is in contact with the upper end surface of the sample;

S5, moving the environmental box 47 containing the test sample by the linkage traction mechanism 6 directly below the axial oil cylinder 21 of the axial loading mechanism 2, and moving the upper shear box 45 and the lower shear box 44 to the area where the horizontal loading mechanism 3 cooperates with the first sample placing mechanism 4;

S6, adjusting the positions of the horizontal shearing cylinder 31 and the lower shearing box 44, the reaction force device 32 and the upper shearing box 45, passing through the first through hole 3112 and the first mounting through hole 442 with a pin, and detachably and fixedly connecting the other end of the lower shearing box 44 with the first connecting block 311, so that the horizontal shearing cylinder 31 is relatively fixed with the lower shearing box 44, passing through the second through hole 3212 and the second mounting through hole 452 with a pin, The other end of the upper shear box 45 is detachably and fixedly connected with the second connecting block 321, so that the upper shear box 45 is relatively fixed with the reaction force device 32;

S7, inserting asbestos into the fit clearance of the avoiding through hole 473 on the environmental box 47;

S8, adjusting the position of the axial oil cylinder 21 so that the driving end of the axial oil cylinder 21 contacts the upper surface of the first pressure head 46;

S9, arranging a displacement sensor at four corners of the upper surface of the first pressure head 46 and at the end of the lower shear box 44;

S10: setting a heating rate and a target temperature by a controller, starting the electric heating wire assembly 48 and the fan assembly 49, heating the interior of the environmental box 47, and maintaining the target temperature for 6 hours after the interior temperature of the environmental box 47 reaches the target temperature;

S11, starting the axial oil cylinder 21 and the horizontal shear oil cylinder 31, and setting the axial load, the shear rate, the shear displacement and the shear cycle times by means of the controller;

S12, recording the axial displacement, shear displacement, shear load and axial load of the sample in the shearing process in real time;

S13, when the horizontal shear oil cylinder 31 completes the cyclic shear displacement, closing the test equipment, and taking out the rock sample to complete the test.

Embodiment 4

Figure 13:
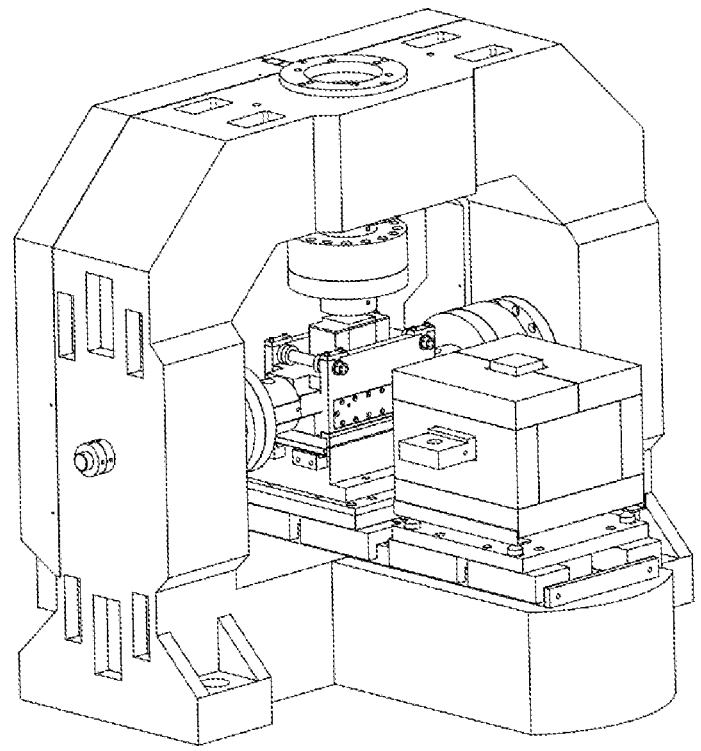
FIG. 13 is a schematic diagram of the state of the second sample placing mechanism of the present disclosure in the test area, wherein the fan assembly and corresponding air duct arranged in the environmental box are not shown, and a part of the detailed mechanism of the environmental box is a brief schematic diagram.

Based on one of FIGS. 1 to 12 and further in combination with FIG. 13, as an alternative embodiment of Embodiment 2, this Embodiment provides a fracture shear seepage test program under constant normal load boundary conditions, including the following steps:

Step 1, placing the second foundation 51 of the second sample placing mechanism 5 on the base plate assembly 65 on the other sliding block 62 of the linkage traction mechanism 6, placing the second roller rows 52 and the lower shear seepage box 53 on the second foundation 51 in sequence, and then placing the lower part of the sample on the third sample accommodating slot 531 of the lower shear seepage box 53, and then installing the first cushion block 532 and the sealing strip on the first cushion block 532 in the third sample accommodating slot 531;

Step 2, inserting a pair of side plates 56 in the lower part into the grooves reserved on both sides of the lower shear seepage box 53 to achieve a relatively constrained connection;

Step 3, placing a sealing strip at the groove of the second cushion block 542 of the upper shear seepage box 54, and then placing the upper shear seepage box 54 and the second cushion block 542 above the lower shear seepage box 53, so that the upper part of the sample is placed in the fourth sample accommodating slot 541 of the upper shear seepage box 54, so that the sample is placed in the accommodating area 58 formed by the closure between the third sample accommodation grooves 531, the fourth sample accommodating slot 541, the first cushion block 532, the second cushion block 542 and a pair of side plates 56;

Step 4, connecting and assembling the capsule pressing plate 562, the sealing capsule 561 and the side plate 56 with bolts, and the upper shear seepage box 54 and the lower shear seepage box 53 are movably constrained between the side plates 56 by the pressing roller block 564 and the pressing roller shaft 563;

Step 5, adjusting the lower shear seepage box 53 to make the sample closely fit with the lower shear seepage box 53;

Step 6, inserting the second pressure head 55 into the avoiding slot at the upper end of the upper shear seepage box 54;

Step 7, moving the second sample placing mechanism 5 containing the sample to a position directly below the axial oil cylinder 21 of the axial loading mechanism 2 by means of the linkage traction mechanism 6;

Step 8, adjusting the positions of the horizontal shear oil cylinder 31 and the lower shear seepage box 53, the reaction force device 32 and the upper shear seepage box 54, passing through the first through hole 3112 and the third mounting through hole 533 via a pin, so that the other end of the lower shear seepage box 53 is detachably and fixedly connected with the first connecting block 311, and the horizontal shear oil cylinder 31 is relatively fixed with the lower shear seepage box 53, passing through the second through hole 3212 and the fourth mounting through hole 543, so that the other end of the upper shear seepage box 54 is detachably and fixedly connected with the second connecting block 321, and the upper shear seepage box 54 is relatively fixed with the reaction force device 32;

Step 9, arranging a displacement sensor at four corners of the upper surface of the second pressure head 55 and at the end of the lower shear seepage box 53;

Step 10, injecting hydraulic oil into the sealing capsule 561;

Step 11, controlling an external seepage medium input device by a controller to inject a seepage medium from the water inlet of the upper shear seepage box 54, measuring water quantity at the water outlet of the lower shear seepage box 53, and calculating a flow rate until a stable seepage flow is reached;

Step 12: setting seepage pressure, axial load, axial stiffness, shear rate and shear displacement by the controller, and recording the axial load, shear load, shear displacement and axial displacement in real time during the shear process;

Step 13, when the horizontal shear oil cylinder 31 moves to the setting displacement, stopping the injection of seepage medium.

Embodiment 5

In combination with one of FIGS. 1 to 12, as an alternative embodiment of embodiment 2, this embodiment provides a program for performing granite uniaxial compression test at high temperature, including the following steps:

Step 1: placing the first sample placing mechanism 4 on the base plate assembly 65 on one slide block 62 of the linkage traction mechanism 6, and then partially disassembling the environmental box 47 so that its interior is opened, and then place the standard cylinder sample into the corresponding position in the environmental box 47;

Step 2: assembling the disassembled part of the environmental box 47, and placing the first pressure head 46 at the avoiding through hole 473 above the environmental box 47 so that the lower end of the first pressure head 46 contacts the upper end surface of the sample;

Step 3: moving the first sample placing mechanism 4 with samples to a position directly below the axial oil cylinder 21 of the axial loading mechanism 2 by means of the linkage traction mechanism 6;

Step 4: setting the heating rate through the controller, starting the electric heating wire assembly 48 and the fan assembly 49, heat the sample indirectly heated by the internal environment of the environmental box 47, and maintaining the target temperature for 4 hours after the internal temperature of the environmental box 47 reaches the target temperature;

Step 5: starting the axial oil cylinder 21, set the movement rate of the axial oil cylinder 21 to 0.06 mm/min through the controller, and then recording the axial displacement and axial load in the compression process in real time;

Step 6: when the axial load-axial displacement curve suddenly drops, stopping the axial oil cylinder 21 and save the data.

Embodiment 6

Figure 14:
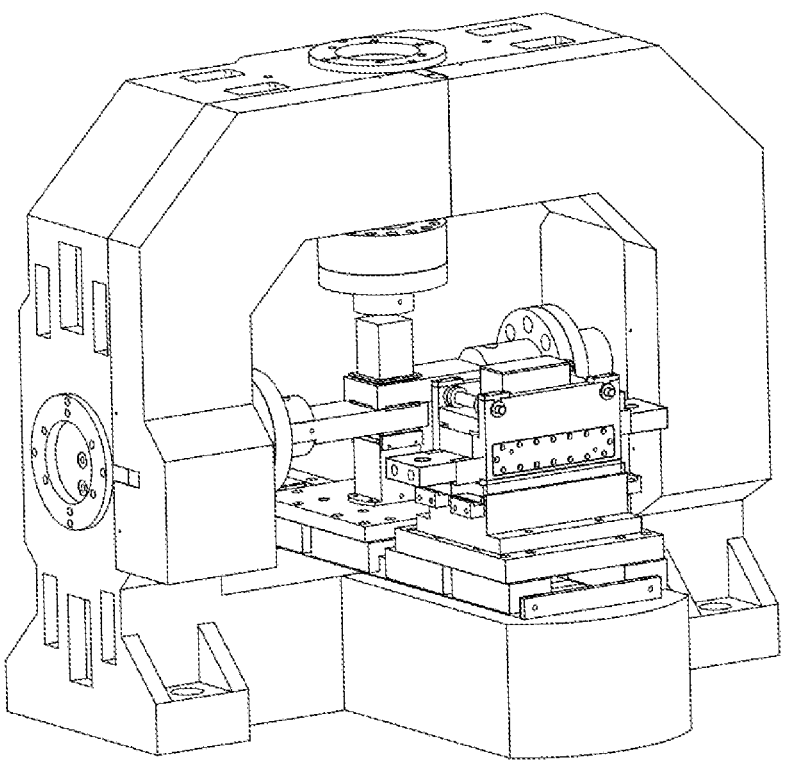
FIG. 14 is a schematic diagram of the first sample placing mechanism of the present disclosure being used without a heating device such as the environmental box.

Based on one of FIGS. 1 to 12 and further in conjunction with FIG. 14, as an alternative embodiment of Embodiment 2, this Embodiment provides a granite fracture shear test under constant normal stiffness boundary conditions at room temperature, including the following steps:

(1) placing the parts of the first sample placing mechanism 4 other than the environmental box 47, the fan assembly 49 and the electric heating wire assembly 48 on the base plate assembly 65 on one of the sliding block 62 of the linkage traction mechanism 6, wherein, placing the granite sample in the lower shear box 44, and then placing the upper shear box 45;

(2) inserting the lower end of the first pressure head 46 into the second sample accommodating slot 451 of the upper shear box 45, and fix the sample in the first sample accommodating slot 441 and the second sample accommodating slot 451;

(3) moving the first sample placing mechanism 4 with the sample by the linkage traction mechanism 6 to a position directly below the axial oil cylinder 21 of the axial loading mechanism 2;

(4) adjusting the positions of the horizontal shear oil cylinder 31 and the lower shear box 44, the reaction force device 32 and the upper shear box 45, and the other end of the lower shear box 44 is detachably and fixedly connected with the first connecting block 311 by passing through the first through hole 3112 and the first mounting through hole 442 via a pin, so that the horizontal shear oil cylinder 31 is relatively fixed with the lower shear box 44, and passes through the second through hole 3212 and the second mounting through hole 452 via a pin, the other end of the upper shear box 45 is detachably and fixedly connected with the second connecting block 321, so that the upper shear box 45 is relatively fixed with the reaction force device 32;

(5) adjusting the position of the axial oil cylinder 21 so that the axial oil cylinder 21 contacts the upper surface of the first pressure head 46;

(6) arranging a displacement sensor at four corners of the upper surface of the first pressure head 46 and at the end of the lower shear box 44;

(7) starting the axial oil cylinder 21 and the horizontal shear oil cylinder 31, and setting the axial load, axial stiffness, shear rate and shear displacement through the controller;

(8) recording the axial displacement, shear displacement, shear load and axial load of the sample in the shearing process in real time;

(9) when the horizontal shear oil cylinder 31 reaches the set shear displacement, closing the test equipment and take out the rock sample.

The above are only partial embodiments of the present disclosure, and do not limit the scope of protection of the present disclosure. Any equivalent device or equivalent process transformation made by using the description of the present disclosure and the attached drawings, or directly or indirectly applied in other relevant technical fields, are similarly included in the scope of patent protection of the present disclosure.

What is claimed is:

1. An underground engineering rock mass shear simulation test device, comprising:

a frame comprising a base and a gantry spanning over the base, wherein a test area is formed between a lower side of the gantry and the base;

an axial loading mechanism, which is set on a lower side of a middle part of the gantry, and is used to provide force loading for test samples in the test area;

a horizontal loading mechanism, which is arranged on both sides of the gantry close to the test area and is used for providing shear force loading to the test samples in the test area;

a first sample placing mechanism and a second sample placing mechanism, which are respectively arranged above the base and are used for placing the test samples;

a linkage traction mechanism, which is arranged on the base and connected with the first sample placing mechanism and the second sample placing mechanism respectively, and used for driving the first sample placing mechanism or the second sample placing mechanism to move into or out of the test area;

a controller, which is connected with the axial loading mechanism, the horizontal loading mechanism and the linkage traction mechanism respectively, and the controller controls the axial loading mechanism, the horizontal loading mechanism and the linkage traction mechanism to start or stop;

wherein the horizontal loading mechanism and the axial loading mechanism have a first matching state and a second matching state with the first sample placing mechanism or the second sample placing mechanism;

in the first matching state, the first sample placing mechanism or the second sample placing mechanism is located in the test area, the axial loading mechanism loads an axial force to the sample in the first sample placing mechanism or the second sample placing mechanism, and the horizontal loading mechanism loads a shear force to the sample in the first sample placing mechanism or the second sample placing mechanism;

in the second matching state, the axial loading mechanism and the horizontal loading mechanism relieve the force loading applied to the first sample placing mechanism or the second sample placing mechanism.

2. The underground engineering rock mass shear simulation test device according to claim 1, wherein the axial loading mechanism comprises an axial oil cylinder, which is installed at a lower side of the middle part of the gantry, a driving end of the axial oil cylinder vertically faces downward and faces a sample located in the test area, the axial oil cylinder is connected to the controller and controlled by the controller to start or stop;

the horizontal loading mechanism comprises:

a horizontal shear oil cylinder, which is arranged on a side of the gantry close to the test area, a driving end of the horizontal shear oil cylinder faces the test area and is used for cooperating with a side of the sample located in the test area and providing horizontal shear force loading, the horizontal shear oil cylinder being connected to the controller and being controlled by the controller to start or stop;

a reaction force device, which is arranged on an other side of the gantry close to the test area and is used for cooperating with an other side of the sample located in the test area;

the linkage traction mechanism comprises:

a linear guide rail, which is installed on the base through a support block, and two ends of the linear guide rail span the test area under the gantry;

a pair of sliding block, which are slidably connected to the linear guide rail, wherein the upper end of each sliding block is connected with a base plate assembly, and the base plate assembly is cooperatively connected with the first sample placing mechanism or the second sample placing mechanism;

a servo motor, which is fixedly connected to one end of the linear guide rail, a driving end thereof faces an other end of the linear guide rail, the servo motor is connected to the controller and controlled by the controller to start or stop;

a speed reducer, wherein a power input end of the speed reducer is connected to a driving end of the servo motor, and a power output end of the speed reducer is connected with a screw rod through a coupling, a end of the screw rod far away from the speed reducer extends to a other end of the linear guide rail;

wherein, a lower ends of each pair of sliding block are fixedly connected with threaded connection blocks connected with the screw rod, and the screw rod is driven by the servo motor to rotate, so that each pair of sliding block drive the first sample placing mechanism and the second sample placing mechanism connected to their upper ends to synchronously translate along a length direction of the linear guide rail, so that the first sample placing mechanism or the second sample placing mechanism are moved into or out of the test area under the gantry.

3. The underground engineering rock mass shear simulation test device according to claim 2, wherein the first sample placing mechanism comprises:

a first foundation, a lower part of which is connected with the base plate assembly on one of the sliding block;

a first roller rows, which is movably disposed on an upper end surface of a first foundation, the upper end surface of the first foundation is provided with a first sink for accommodating the first roller rows, an upper side of the first roller rows is flush with or higher than the upper end of the first sink;

a first base plate, which is arranged above the first foundation, and a lower end surface of the first base plate is in contact with the upper side of the first roller rows;

a lower shear box, one end of which is placed on the upper end surface of the first base plate, and one end of the lower shear box is further provided with a first sample accommodating slot through a upper and a lower end surfaces of the lower shear box, a structure outline of the first sample accommodating slot is adapted to a lower part of the sample; an other end of the lower shear box is provided with a first mounting through hole and is used for cooperating with the horizontal shear oil cylinder, the horizontal shear oil cylinder is connected with a first connecting block, the first connecting block is provided with a first U-shaped groove that is clamped and cooperated with an other end of the lower shear box, the first U-shaped groove is provided with a first through hole that is adapted to and mutually cooperated with the first mounting through hole, and after the other end of the lower shear box is clamped and cooperated with the first U-shaped groove, a pin passes through the first through hole and the first mounting through hole, so that the other end of the lower shear box is detachably and fixedly connected with the first connecting block;

an upper shear box, one end of which is placed on an upper end surface of one end of the lower shear box, one end of the upper shear box is provided with a second sample accommodating slot through the upper and lower end surfaces thereof, and the structure outline of the second sample accommodating slot is adapted to the upper part of the sample; an other end of the upper shear box is provided with a second mounting through hole for cooperating with the reaction force device, the reaction force device is connected with a second connecting block, the second connecting block is provided with a second U-shaped groove for engaging and cooperating with an other end of the upper shear box, the second U-shaped groove is provided with a second through hole adapted to and cooperating with the second mounting through hole, and after the other end of the upper shear box is engaged and cooperating with the second U-shaped groove, a pin passes through the second through hole and the second mounting through hole, so that the other end of the upper shear box is detachably and fixedly connected with the second connecting block;

a first pressure head, a lower end of which is movably inserted into the second sample accommodating slot of the upper shear box and cooperates with the first base plate, and the sample is constrained and fixed in the first sample accommodating slot and the second sample accommodating slot; an upper end of the first pressure head is used for cooperating with the driving end of the axial oil cylinder;

an environmental box, which is a detachable box structure having an accommodating cavity formed inside and the accommodating cavity accommodates one end of the lower shear box and the upper shear box, two sides of the environmental box face the upper shear box and the lower shear box respectively, the upper end of the environmental box is provided with an avoiding through hole for passing through an other end of the first pressure head;

an electric heating wire assembly, which is arranged in the accommodation cavity and connected with the controller, and controlled by the controller to start or stop;

a fan assembly, which is arranged on one side of an environmental box, and an wind output end of the environmental box corresponding to the fan assembly is provided with an air duct connected to the accommodation cavity of the environmental box, the fan assembly is used for guiding and blowing air heated by the electric heating wire assembly to a surface of the sample, so as to realize a temperature adjustment of the sample;

wherein the first pressure head and the lower shear box are uniformly provided with more than one displacement sensors, and the upper shear box, the lower shear box and the bottom of the first pressure head are all provided with reserved holes for threading temperature sensors to the surface of the sample.

4. The underground engineering rock mass shear simulation test device according to claim 3, wherein the second sample placing mechanism comprises:

a second foundation, a lower part of which is connected with a base plate assembly on another sliding block;

a second roller rows, which is movably disposed on an upper end surface of the second foundation, an upper end surface of the second foundation is provided with a second sink for accommodating the second roller rows, an upper side of the second roller rows is flush with or higher than an upper end of the second sink;

a lower shear seepage box, one end of which is placed on an upper end surface of the second foundation, a lower end surface of one end of the lower shear seepage box is fitted with the second roller rows, a third sample accommodating slot is also provided on an upper end surface of one end of the lower shear seepage box, the third sample accommodating slot is an U-shaped slot open on both sides, and a first cushion block is provided on a side away from an other end of the lower shear seepage box, an upper end surface of the first cushion block is flush with an upper end surface of the lower shear seepage box; an other end of the lower shear seepage box is provided with a third mounting through hole and is used for cooperating with a horizontal shear oil cylinder; when the horizontal shear oil cylinder cooperates with the lower shear seepage box, an other end of the lower shear seepage box is detachably and fixedly connected with the first connecting block by passing through the first through hole and the third mounting through hole;

an upper shear seepage box, one end of which is placed on an upper end surface of one end of the lower shear box, and an lower end surface of one end of the lower shear seepage box is in contact with an upper end surface of the first cushion block, a lower end surface of one end of the upper shear seepage box is provided with a fourth sample accommodating slot, the fourth sample accommodating slot is a U-shaped slot open on both sides, and an other side away from an other end of the upper shear seepage box is provided with a second cushion block, a lower end surface of the second cushion block is flush with a lower end surface of the upper shear seepage box, and an upper end surface of one end of the lower shear seepage box is contacted with the lower end surface of the second cushion block; an other end of the upper shear seepage box is provided with a fourth mounting through hole and is used for cooperating with the reaction force device, when the reaction force device cooperates with the upper shear seepage box, an other end of the upper shear seepage box is detachably and fixedly connected with the second connecting block by passing through the second through hole and the fourth mounting through hole;

a pair of side plates, which are arranged oppositely on both sides of the upper shear seepage box and the lower shear seepage box, and constraining the upper shear seepage box and the lower shear seepage box between a pair of side plates, wherein the third sample accommodating slot, the fourth sample accommodating slot, the first cushion block, the second cushion block and the pair of side plates enclose to form a accommodating area for accommodating a sample, and both sides of the accommodating area are provided with a sealing capsule, an end surfaces of the first cushion block and the upper shear seepage box is provided with a sealing groove, and an end surfaces of the second cushion block and the lower shear seepage box is also provided with a sealing groove, the sealing grooves are embedded with a sealing strip, in addition, one end of the upper shear seepage box is also provided with a water inlet penetrating into the accommodating area, and one end of the lower shear seepage box is also provided with a water outlet penetrating into the accommodating area; the upper ends of the pair of side plates are detachably connected to a pair of oppositely arranged pressing roller shafts, both ends of the pressing roller shafts are respectively connected to the pair of side plates, and the pressing roller shafts are sleeved with annular pressing roller blocks for cooperating with the upper end surfaces of the upper shear seepage box; the pair of side plates are also provided with a sealing capsule pressing plate matched with the sealing capsule according to the sealing capsule;

a second pressure head, the lower end of which is movably inserted into the fourth sample accommodating slot of the upper shear seepage box and abuts against the sample placed in the accommodating cavity, the upper end of the upper shear seepage box being provided with an avoiding slot for the second pressure head to insert, and the upper end of the second pressure head being used for cooperating with the drive end of an axial oil cylinder;

wherein the second pressure head and the lower shear seepage box are uniformly provided with more than one displacement sensor.

5. An underground engineering rock mass shear simulation test method, comprising the underground engineering rock mass shear simulation test device according to claim 4, used for performing cyclic shear test at high temperature, fracture shear seepage test, granite uniaxial compression test at high temperature and/or granite fracture shear test;

the underground engineering rock mass shear simulation test method comprising:

setting constant normal load boundary conditions and constant normal stiffness boundary conditions at room temperature by the controller;

performing cyclic shear test at high temperature and fracture shear seepage test under constant normal load boundary conditions; a heating temperature of the cyclic shear test at high temperature is room temperature –400° C. with a precision of ±2° C. and a heating rate of 5° C./h-400° C./h;

performing granite fracture shear tests at room temperature under constant normal stiffness boundary conditions.

6. The underground engineering rock mass shear simulation test method according to claim 5, wherein performing the cyclic shear test at high temperature under constant normal load boundary conditions comprises following steps:

S1, placing the first foundation and the environmental box of the first sample placing mechanism on the base plate assembly on one of the sliding block of the linkage traction mechanism, partially disassembling the environmental box so that its interior is opened, and successively placing the roller rows, the base plate and the lower shear box on the end of the first foundation in the accommodation cavity;

S2, placing a lower part of a sample of rock into the first sample accommodating slot of the lower shear box;

S3, placing the upper shear box above the lower shear box so that the upper part of the sample is placed in the second sample accommodating slot of the upper shear box, placing the temperature sensor from the reserved holes of the upper shear box, the lower shear box and the first pressure head to an upper surface, a front surface and a left surface of the sample, and fixing the temperature sensor in the reserved holes with asbestos;

S4, assembling a disassembled part of the environmental box, and placing the first pressure head at the through hole above the environmental box so that a lower end of the first pressure head contacts the upper end surface of the sample;

S5: moving the environmental box with the sample to a position directly below the axial oil cylinder of the axial loading mechanism by the linkage traction mechanism, and at the same time, moving the upper shear box and the lower shear box to the area where the horizontal loading mechanism cooperates with the first sample placing mechanism;

S6, adjusting positions of the horizontal shear oil cylinder and the lower shear box, the reaction force device and the upper shear box, passing through the first through hole and the first mounting through hole via a pin, so that the other end of the lower shear box is detachably and fixedly connected with the first connecting block, and the horizontal shear oil cylinder is relatively fixed with the lower shear box, passing through the second through hole and the second mounting through hole through the pin, so that the other end of the upper shear box is detachably and fixedly connected with the second connecting block, and the upper shear box is fixed with the reaction force device relatively;

S7, inserting asbestos into a fitting clearance of the avoiding through hole on the environmental box;

S8: adjusting a position of the axial oil cylinder so that the driving end of the axial oil cylinder contacts the upper surface of the first pressure head;

S9, arranging the displacement sensor at four corners of the upper surface of the first pressure head and at the end of the lower shear box;

S10: setting a heating rate and a target temperature by the controller, starting the electric heating wire assembly and the fan assembly, heating the interior of the environmental box, and maintaining the target temperature for 6 hours after the temperature inside the environmental box reaches the target temperature;

S11: starting the axial oil cylinder and the horizontal shear oil cylinder, and setting an axial load, shear rate, shear displacement and shear cycle times by means of the controller;

S12, recording an axial displacement, shear displacement, shear load and axial load of the sample in the shearing process in real time;

S13, when the horizontal shear oil cylinder completes the cyclic shear displacement, closing the test equipment, taking out the sample of rock to complete the test.

7. The underground engineering rock mass shear simulation test method according to claim 5, wherein performing the fracture shear seepage test under constant normal load boundary conditions comprises following steps:

step 1: placing the second foundation of the second sample placing mechanism on the base plate assembly on the other sliding block of the linkage traction mechanism, placing the second roller rows and the lower shear seepage box on the second foundation in sequence, and then placing the lower part of the sample on the third sample accommodating slot of the lower shear seepage box, and then installing the first cushion block and the sealing strip on the first cushion block in the third sample accommodating slot;

step 2: inserting the lower part of the pair of side plates into the reserved grooves on both sides of the lower shear seepage box to realize a relative constraint connection;

step 3: placing the sealing strip at the sealing groove of the second cushion block of the upper shear seepage box, and then placing the upper shear seepage box and the second cushion block above the lower shear seepage box, so that the upper part of the sample is placed in the fourth sample accommodating slot of the upper shear seepage box, so that the sample is placed in the accommodating area formed by the closure of the third sample accommodating slot, the fourth sample accommodating slot, the first cushion block, the second cushion block and the pair of side plates;

step 4: connecting and assembling the capsule pressing plate, the sealing capsule and the side plates by bolts, and the upper shear seepage box and the lower shear seepage box are movably constrained between the side plates by the pressing roller block and the pressing roller shaft;

step 5: adjusting the lower shear seepage box to make the sample closely fit with the lower shear seepage box;

step 6: placing a second pressure head at the avoiding slot at the upper end of the upper shear seepage box;

step 7: moving the second sample placing mechanism with the sample to a position directly below the axial oil cylinder of the axial loading mechanism by the linkage traction mechanism;

step 8: adjusting the positions of the horizontal shear oil cylinder and the lower shear seepage box, the reaction force device and the upper shear seepage box, passing through the first through hole and the third mounting through hole via a pin, and detachably and fixedly connecting the other end of the lower shear seepage box with the first connecting block, so that the horizontal shear oil cylinder is relatively fixed with the lower shear seepage box, passing through the second through hole and the fourth mounting through hole via a pin, the other end of the upper shear seepage box is detachably and fixedly connected with the second connecting block, so that the upper shear seepage box is relatively fixed with the reaction force device;

step 9, arranging the displacement sensor at four corners of the upper surface of the second pressure head and at the end of the lower shear seepage box;

step 10, injecting hydraulic oil into the sealing capsule;

step 11, controlling an external seepage medium input device by the controller to inject a seepage medium from the water inlet of the upper shear seepage box, measuring water quantity at the water outlet of the lower shear seepage box, and calculating a flow rate until a stable seepage flow is reached;

step 12: setting seepage pressure, axial load, axial stiffness, shear rate and shear displacement by the controller, and recording the axial load, shear load, shear displacement and axial displacement in real time during the shear process;

step 13: when the horizontal shear oil cylinder moves to the setting shear displacement, stopping injecting the seepage medium.

8. The underground engineering rock mass shear simulation test method according to claim 5, wherein performing granite uniaxial compression test at high temperature comprises following steps:

step 1: placing the loading mechanism of the first sample on the base plate assembly on one of the sliding block of the linkage traction mechanism, and then partially disassembling the environmental box so that its interior is opened, and then placing a standard cylinder sample into the corresponding position in the environmental box;

step 2: assembling the disassembled part of the environmental box, and placing the first pressure head at the through hole above the environmental box to make the lower end of the first pressure head contact with the upper end surface of the sample;

step 3: moving the first sample placing mechanism with samples to a position directly below the axial oil cylinder of the axial loading mechanism through the linkage traction mechanism;

step 4: setting the heating rate through the controller, starting the electric heating wire assembly and the fan assembly, heating the sample indirectly heated by the internal environment of the environmental box, and maintaining the target temperature for 4 hours after the internal temperature of the environmental box reaches the target temperature;

step 5: starting the axial oil cylinder, setting the movement rate of the axial oil cylinder as 0.06 mm/min through the controller, and then recording the axial displacement and axial load in a compression process in real time;

step 6: when the axial load-axial displacement curve suddenly drops, stopping the axial oil cylinder movement and saving data.

9. The underground engineering rock mass shear simulation test method according to claim 5, wherein performing granite fracture shear test under constant normal stiffness boundary conditions at room temperature comprises following steps:

(1) placing the parts of the first sample placing mechanism other than the environmental box, fan assembly and electric heating wire assembly on the base plate assembly on one of the sliding block of the linkage traction mechanism, firstly placing the granite sample in the lower shear box, and then placing the upper shear box;

(2) inserting the lower end of the first pressure head into the second sample accommodating slot of the upper shear box, and restraining and fix the sample in the first sample accommodating slot and the second sample accommodating slot;

(3) moving the first sample placing mechanism with samples to a position directly below the axial oil cylinder of the axial loading mechanism through the linkage traction mechanism;

(4) adjusting the positions of the horizontal shear oil cylinder, the lower shear box, the reaction force device and the upper shear box, connecting the other end of the lower shear box is detachably and fixedly with the first connecting block via a pin passing through the first through hole and the first mounting through hole, so that the horizontal shear oil cylinder is relatively fixed with the lower shear box, the other end of the upper shear box is detachably and fixedly connected with the second connecting block through the second through hole and the second mounting through hole through pin passing through the second through hole, fixing the upper shear box relative to the reaction force device;

(5) adjusting the position of the axial oil cylinder so that the axial oil cylinder contacts the upper surface of the first pressure head;

(6) arranging displacement sensors at four corners of the upper surface of the first pressure head and at the end of the lower shear box;

(7) starting the axial oil cylinder and the horizontal shear oil cylinder, and setting the axial load, axial stiffness, shear rate and shear displacement through the controller;

(8) recording the axial displacement, shear displacement, shear load and axial load of the sample in the shearing process in real time;

(9) when the horizontal shear oil cylinder reaches the setting shear displacement, closing the test equipment and taking out the rock sample.

10. A testing machine, wherein the testing machine implements the underground engineering rock mass shear simulation test method for performing cyclic shear test at high temperature, fracture shear seepage test, granite uniaxial compression test at high temperature and/or granite fracture shear test;

the underground engineering rock mass shear simulation test method comprising:

setting constant normal load boundary conditions and constant normal stiffness boundary conditions at room temperature by the controller;

performing cyclic shear test at high temperature and fracture shear seepage test under constant normal load boundary conditions; a heating temperature of the cyclic shear test at high temperature is room temperature –400° C. with a precision of ±2° C. and a heating rate of 5° C./h-400° C./h;

performing granite fracture shear tests at room temperature under constant normal stiffness boundary conditions.

11. The testing machine according to claim 10, wherein performing the cyclic shear test at high temperature under constant normal load boundary conditions comprises following steps:

S1, placing the first foundation and the environmental box of the first sample placing mechanism on the base plate assembly on one of the sliding block of the linkage traction mechanism, partially disassembling the environmental box so that its interior is opened, and successively placing the roller rows, the base plate and the lower shear box on the end of the first foundation in the accommodation cavity;

S2, placing a lower part of a sample of rock into the first sample accommodating slot of the lower shear box;

S3, placing the upper shear box above the lower shear box so that the upper part of the sample is placed in the second sample accommodating slot of the upper shear box, placing the temperature sensor from the reserved holes of the upper shear box, the lower shear box and the first pressure head to an upper surface, a front surface and a left surface of the sample, and fixing the temperature sensor in the reserved holes with asbestos;

S4, assembling a disassembled part of the environmental box, and placing the first pressure head at the through hole above the environmental box so that a lower end of the first pressure head contacts the upper end surface of the sample;

S5: moving the environmental box with the sample to a position directly below the axial oil cylinder of the axial loading mechanism by the linkage traction mechanism, and at the same time, moving the upper shear box and the lower shear box to the area where the horizontal loading mechanism cooperates with the first sample placing mechanism;

S6, adjusting positions of the horizontal shear oil cylinder and the lower shear box, the reaction force device and the upper shear box, passing through the first through hole and the first mounting through hole via a pin, so that the other end of the lower shear box is detachably and fixedly connected with the first connecting block, and the horizontal shear oil cylinder is relatively fixed with the lower shear box, passing through the second through hole and the second mounting through hole through the pin, so that the other end of the upper shear box is detachably and fixedly connected with the second connecting block, and the upper shear box is fixed with the reaction force device relatively;

S7, inserting asbestos into a fitting clearance of the avoiding through hole on the environmental box;

S8: adjusting a position of the axial oil cylinder so that the driving end of the axial oil cylinder contacts the upper surface of the first pressure head;

S9, arranging the displacement sensor at four corners of the upper surface of the first pressure head and at the end of the lower shear box;

S10: setting a heating rate and a target temperature by the controller, starting the electric heating wire assembly and the fan assembly, heating the interior of the environmental box, and maintaining the target temperature for 6 hours after the temperature inside the environmental box reaches the target temperature;

S11: starting the axial oil cylinder and the horizontal shear oil cylinder, and setting an axial load, shear rate, shear displacement and shear cycle times by means of the controller;

S12, recording an axial displacement, shear displacement, shear load and axial load of the sample in the shearing process in real time;

S13, when the horizontal shear oil cylinder completes the cyclic shear displacement, closing the test equipment, taking out the sample of rock to complete the test.

12. The testing machine according to claim 10, wherein performing the fracture shear seepage test under constant normal load boundary conditions comprises following steps:

step 1: placing the second foundation of the second sample placing mechanism on the base plate assembly on the other sliding block of the linkage traction mechanism, placing the second roller rows and the lower shear seepage box on the second foundation in sequence, and then placing the lower part of the sample on the third sample accommodating slot of the lower shear seepage box, and then installing the first cushion block and the sealing strip on the first cushion block in the third sample accommodating slot;

step 2: inserting the lower part of the pair of side plates into the reserved grooves on both sides of the lower shear seepage box to realize a relative constraint connection;

step 3: placing the sealing strip at the sealing groove of the second cushion block of the upper shear seepage box, and then placing the upper shear seepage box and the second cushion block above the lower shear seepage box, so that the upper part of the sample is placed in the fourth sample accommodating slot of the upper shear seepage box, so that the sample is placed in the accommodating area formed by the closure of the third sample accommodating slot, the fourth sample accommodating slot, the first cushion block, the second cushion block and the pair of side plates;

step 4: connecting and assembling the capsule pressing plate, the sealing capsule and the side plates by bolts, and the upper shear seepage box and the lower shear seepage box are movably constrained between the side plates by the pressing roller block and the pressing roller shaft;

step 5: adjusting the lower shear seepage box to make the sample closely fit with the lower shear seepage box;

step 6: placing a second pressure head at the avoiding slot at the upper end of the upper shear seepage box;

step 7: moving the second sample placing mechanism with the sample to a position directly below the axial oil cylinder of the axial loading mechanism by the linkage traction mechanism;

step 8: adjusting the positions of the horizontal shear oil cylinder and the lower shear seepage box, the reaction force device and the upper shear seepage box, passing through the first through hole and the third mounting through hole via a pin, and detachably and fixedly connecting the other end of the lower shear seepage box with the first connecting block, so that the horizontal shear oil cylinder is relatively fixed with the lower shear seepage box, passing through the second through hole and the fourth mounting through hole via a pin, the other end of the upper shear seepage box is detachably and fixedly connected with the second connecting block, so that the upper shear seepage box is relatively fixed with the reaction force device;

step 9, arranging the displacement sensor at four corners of the upper surface of the second pressure head and at the end of the lower shear seepage box;

step 10, injecting hydraulic oil into the sealing capsule;

step 11, controlling an external seepage medium input device by the controller to inject a seepage medium from the water inlet of the upper shear seepage box, measuring water quantity at the water outlet of the lower shear seepage box, and calculating a flow rate until a stable seepage flow is reached;

step 12: setting seepage pressure, axial load, axial stiffness, shear rate and shear displacement by the controller, and recording the axial load, shear load, shear displacement and axial displacement in real time during the shear process;

step 13: when the horizontal shear oil cylinder moves to the setting shear displacement, stopping injecting the seepage medium.

13. The testing machine according to claim 10, wherein performing granite uniaxial compression test at high temperature comprises following steps:

step 1: placing the loading mechanism of the first sample on the base plate assembly on one of the sliding block of the linkage traction mechanism, and then partially disassembling the environmental box so that its interior is opened, and then placing a standard cylinder sample into the corresponding position in the environmental box;

step 2: assembling the disassembled part of the environmental box, and placing the first pressure head at the through hole above the environmental box to make the lower end of the first pressure head contact with the upper end surface of the sample;

step 3: moving the first sample placing mechanism with samples to a position directly below the axial oil cylinder of the axial loading mechanism through the linkage traction mechanism;

step 4: setting the heating rate through the controller, starting the electric heating wire assembly and the fan assembly, heating the sample indirectly heated by the internal environment of the environmental box, and maintaining the target temperature for 4 hours after the internal temperature of the environmental box reaches the target temperature;

step 5: starting the axial oil cylinder, setting the movement rate of the axial oil cylinder as 0.06 mm/min through the controller, and then recording the axial displacement and axial load in a compression process in real time;

step 6: when the axial load-axial displacement curve suddenly drops, stopping the axial oil cylinder movement and saving data.

14. The testing machine according to claim 10, wherein performing granite fracture shear test under constant normal stiffness boundary conditions at room temperature comprises following steps:

(1) placing the parts of the first sample placing mechanism other than the environmental box, fan assembly and electric heating wire assembly on the base plate assembly on one of the sliding block of the linkage traction mechanism, firstly placing the granite sample in the lower shear box, and then placing the upper shear box;

(2) inserting the lower end of the first pressure head into the second sample accommodating slot of the upper shear box, and restraining and fix the sample in the first sample accommodating slot and the second sample accommodating slot;

(3) moving the first sample placing mechanism with samples to a position directly below the axial oil cylinder of the axial loading mechanism through the linkage traction mechanism;

(4) adjusting the positions of the horizontal shear oil cylinder, the lower shear box, the reaction force device and the upper shear box, connecting the other end of the lower shear box is detachably and fixedly with the first connecting block via a pin passing through the first through hole and the first mounting through hole, so that the horizontal shear oil cylinder is relatively fixed with the lower shear box, the other end of the upper shear box is detachably and fixedly connected with the second connecting block through the second through hole and the second mounting through hole through pin passing through the second through hole, fixing the upper shear box relative to the reaction force device;

(5) adjusting the position of the axial oil cylinder so that the axial oil cylinder contacts the upper surface of the first pressure head;

(6) arranging displacement sensors at four corners of the upper surface of the first pressure head and at the end of the lower shear box;

(7) starting the axial oil cylinder and the horizontal shear oil cylinder, and setting the axial load, axial stiffness, shear rate and shear displacement through the controller;

(8) recording the axial displacement, shear displacement, shear load and axial load of the sample in the shearing process in real time;

(9) when the horizontal shear oil cylinder reaches the setting shear displacement, closing the test equipment and taking out the rock sample.

* * * * *